(12) United States Patent
Straessler et al.

(10) Patent No.: US 8,382,700 B2
(45) Date of Patent: Feb. 26, 2013

(54) MEDICAL DEVICE FOR GLUCOSE MONITORING OR REGULATION

(75) Inventors: Sigfrid Straessler, St-Saphorin-sur-Morges (CH); Uwe Beyer, Olten (CH)

(73) Assignee: Sensile Pat AG, Hagendorf (CH)

( * ) Notice: Subject to any disclaimer, the term of this patent is extended or adjusted under 35 U.S.C. 154(b) by 244 days.

(21) Appl. No.: 12/681,904

(22) PCT Filed: Oct. 22, 2008

(86) PCT No.: PCT/IB2008/054348
§ 371 (c)(1),
(2), (4) Date: Apr. 7, 2010

(87) PCT Pub. No.: WO2009/053911
PCT Pub. Date: Apr. 30, 2009

(65) Prior Publication Data
US 2010/0234830 A1   Sep. 16, 2010

(30) Foreign Application Priority Data
Oct. 23, 2007 (EP) .................................. 07020684

(51) Int. Cl.
*A61N 1/08* (2006.01)
(52) U.S. Cl. ..... 604/65; 604/504; 604/891.1; 604/892.1

(58) Field of Classification Search .................. 604/504, 604/505, 65–67, 890.1, 891.1; 210/96.2, 210/500.21
See application file for complete search history.

(56) References Cited

U.S. PATENT DOCUMENTS
4,445,885 A * 5/1984 Kifune .......................... 604/28
5,062,841 A * 11/1991 Siegel ........................ 604/891.1

FOREIGN PATENT DOCUMENTS
WO  WO 89/01794  3/1989

OTHER PUBLICATIONS
M. Tang et al, A reversibe hydrogel membrane for controlling the delivery of macromolecules, Biotechnology and Bioengineering, vol. 82, Issue 1, Apr. 5, 2003.*
Written Opinion in International Application No. PCT/IB2008/054348, May 5, 2009, pp. 1-7.

* cited by examiner

*Primary Examiner* — Laura Bouchelle
(74) *Attorney, Agent, or Firm* — Saliwanchik, Lloyd & Eisenschenk

(57) ABSTRACT

A medical device comprising a pressure generating means adapted to deliver a liquid, a sensor adapted to measure a flow resistance, and an implantable member comprising an analyte responsive porous membrane which reversibly changes its porosity subject to changes in analyte concentration occurring in the solution surrounding the implantable member. The analyte may in particular be glucose. The medical device may also be used for drug administration.

26 Claims, 7 Drawing Sheets

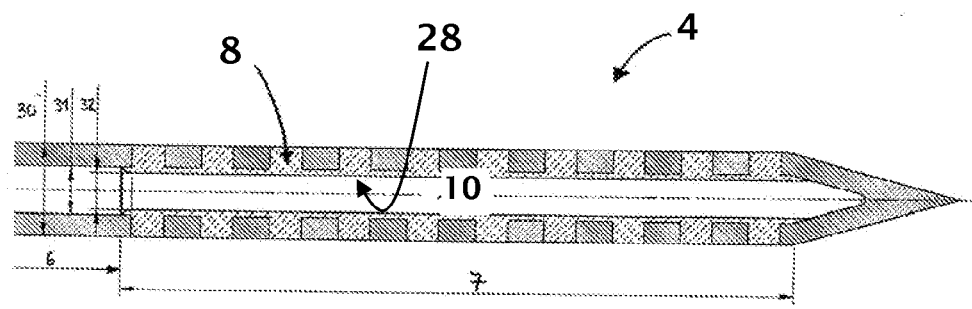
FIG. 2a
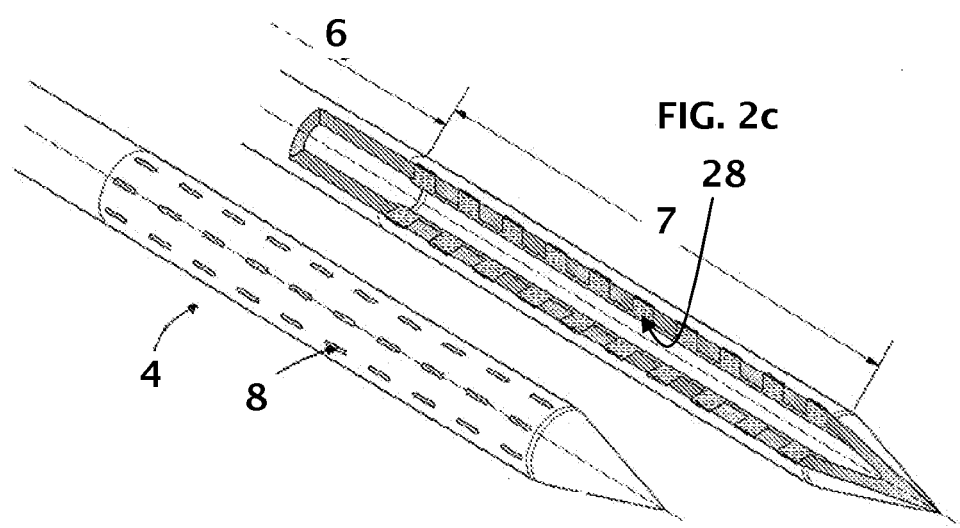
FIG. 2c
FIG 2b

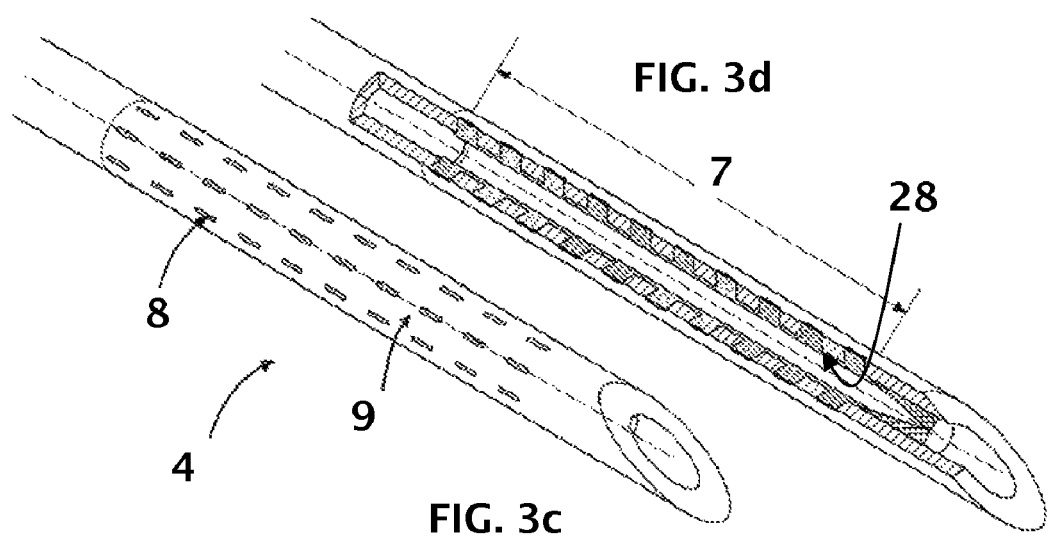

US 8,382,700 B2

MEDICAL DEVICE FOR GLUCOSE MONITORING OR REGULATION

CROSS-REFERENCE TO RELATED APPLICATION

This application is the U.S. national stage application of International Patent Application No. PCT/IB2008/054348, filed Oct. 22, 2008, the disclosure of which is hereby incorporated by reference in its entirety, including all figures, tables and amino acid or nucleic acid sequences.

The present invention relates to a medical device suitable for analyte monitoring and for drug delivery, in particular for monitoring of glucose and for the treatment of patients with diabetes.

Different medical devices intended for the treatment of patients with diabetes have previously been described: Separate glucose sensors (e.g. electrochemical, viscosimetric, or optical sensors), separate medication delivery devices (e.g. insulin pumps and insulin pens) as well as so-called closed loop systems, i.e. systems integrating glucose sensor and medication delivery. The latter ideally mimics the function of the pancreas, i.e. medication capable of controlling blood glucose level is released subject to blood glucose concentration.

A medical system that combines a glucose monitoring unit with a drug infusion unit is described in patent application US 2006/0224141. In this medical system, the analyte monitoring unit is separated from the medication infusion unit. The analyte sensor is based on using electrodes in order to determine a change in electric resistance subject to a change of the analyte concentration.

U.S. Pat. No. 5,569,186A discloses another closed loop system, where parts of the medical system are completely implanted in the patient.

Another closed loop system is described in patent application WO 03047426A1, where an at least partially implanted glucose sensor is in communication with an injection pen, whereas the user can adjust the dose to be injected based on the glucose concentration measured by the glucose sensor.

The above described closed loop systems for controlling medication infusion consist of at least two separated units, connected through an electronic interface.

WO 89/01794 discloses an implantable glucose sensor for a one part integrated drug delivery system. The sensor includes a liquid infusate, which is put under pressure and flows through a catheter. One section of the catheter contains a microporous membrane, where the concentration of the glucose present in the infusate is equilibrated with a response time between several minutes up to one hour. The equilibrated infusate then flows through a chemical valve which consists of a matrix containing concanavalin A, and dextran molecules. The matrix in the chemical valve changes its porosity subject to the glucose concentration present in the infusate, thus regulating the amount of infusate flowing into the body of a patient.

When the system, as disclosed in WO 89/01794, is employed to solely monitor the concentration of glucose in the surrounding medium, the catheter contains an additional glucose sensor, such as an enzyme electrode, a fuel cell, or an affinity sensor, whereas the chemical valve is not present. Further proposed is a stand-alone sensor, in which the pressure in the infusate is determined before and after the infusate has passed the chemical valve matrix, whereas the pressure-drop across the chemical valve matrix is inversely proportional to the glucose concentration in the equilibrated infusate.

In order to control the blood glucose level in a patient with diabetes, it is necessary to obtain results quickly in order to adjust the delivery of drugs. That is why response times of components within the glucose sensor are a crucial factor for a successful drug delivery program. If, as described in WO 89/01794, an equilibration region has a response time of up to one hour, and a matrix contained in a chemical valve has an additional response time, the drug administration is adjusted to a blood glucose value that is no longer present in the patient, and thus the regulation of the patient's blood glucose level will not be optimal.

Further, if the matrix that determines the pore size is in a fluent state, i.e. new components (such as dextran molecules) arriving with the infusate replace components that are washed away with the infusate into the patient's body, components that do not contribute to the treatment may enter the patient's body (concanavalin A is a toxic compound). The matrix is likely to have changed characteristics over time, as the replacement of new components may not take place in an evenly distributed manner (clusters are likely to occur at the entry of the matrix where the infusate with new components arrives at first).

An object of this invention is to provide a medical device for the measurement of analyte levels in a patient that is rapid and accurate.

Another object of this invention is to provide a medical device that enables fine and timely regulation of the analyte levels.

A particular object of this invention is to provide a medical device for the measurement of blood glucose levels in a patient that is rapid and accurate, and that enables fine and timely regulation of blood glucose levels.

Another particular object of this invention is to provide a medical device for the regulation of blood glucose levels in a patient that provides rapid, accurate and timely regulation of blood glucose levels.

It would be advantageous to provide a medical device for analyte measurement and/or regulation that is compact, light weight and economical to manufacture.

It would be advantageous to provide a medical device for analyte measurement and/or regulation that is convenient and easy to wear.

Objects of this invention have been achieved by providing a medical device for measuring an analyte concentration according to claim 1, and by providing a method for measuring analyte concentration and regulating analyte levels according to claim 12.

Disclosed herein is a medical device comprising a pressure generating means adapted to deliver a liquid. The medical device further comprises a sensor adapted to measure a flow resistance, and an implantable member comprising a porous membrane. Said porous membrane reversibly changes its porosity subject to changes in analyte concentration that occur in the medium surrounding the implantable member. In particular, the analyte may be glucose.

The liquid according to one embodiment of the present invention contains a drug capable of influencing an analyte level (for instance a blood glucose level) in a patient, such that the medical device may also be used for drug administration.

Also disclosed is a method of measuring an analyte concentration comprising: providing a medical device comprising an implantable member with a porous membrane which changes its porosity subject to changes in analyte concentration occurring in the solution surrounding the implantable member; injecting discrete volume of liquid towards said porous membrane; measuring a value correlated to a resistance against flow of said liquid through said porous membrane; and calculating an analyte concentration based on the measured value correlated to flow resistance through the porous membrane.

In case the analyte is glucose said method may, according to an embodiment, further comprise the step of delivering one or more drugs capable of influencing a blood glucose level in a patient according to the measured glucose concentration.

According to a preferred embodiment of this invention, the pressure generating means comprises a pump and a reservoir. The pump delivers accurate predefined quantities of liquid from the reservoir towards the implantable member. Such pumps are well known in the prior art. Whilst remaining within the spirit of the invention, different types of pumps may be used, such as piston pumps, or peristaltic pumps. One pump especially preferred is described in EP 1527793A1, which is introduced herein by reference. Such a pump is both small in size, as well as capable of delivering precisely small amounts of liquid. The reservoir may be a collapsible reservoir with flexible walls, or a reservoir that has a fixed form, such as standard ampoules made of glass with a movable plug.

According to an embodiment of this invention, the pump pulls the fluid out of the reservoir and delivers the fluid towards the implantable member. According to another preferred embodiment of this invention, the reservoir is put under pressure so that the liquid is forced towards the pump. This can be achieved in various ways, for example by forcing a plug forward in a glass ampoule reservoir, or by applying a force on a sidewall of a flexible reservoir, or by employing a second reservoir filled with pressurized gas that exerts pressure on the reservoir filled with liquid.

If the liquid in the reservoir is put under pressure, then a valve can be used instead of the pump. Valves that open and close in order to deliver precise amounts of liquid have been described in the prior art and are well known to the skilled person in this field of technology.

Advantageously, the liquid is delivered in discrete (i.e. non continuous) amounts towards the porous membrane. In between the delivery of discrete amounts, the glucose concentration in the porous membrane is adjusted to the glucose concentration present in the surrounding solution by means of diffusion. Once the glucose concentration in the porous membrane corresponds to the glucose concentration in the surrounding solution, the flow resistance measured when the liquid is forced through the porous membrane serves as a measure for the glucose concentration present in the surrounding solution.

In a preferred embodiment, the sensor adapted to measure a flow resistance comprises a flexible membrane bounding a chamber, the membrane being elastically displaced upon injection of a pre-determined volume of liquid in the chamber from the pressure generating means. During its relaxation, the flexible membrane generates a pressure that conveys the liquid towards the porous membrane contained in the implantable member. The flexible membrane will relax into its original position at a rate that depends on the membrane's porosity, which itself depends on the glucose concentration in the surrounding solution. The elastic membrane relaxation (or amplitude decay) rate serves as a measure of the flow resistance. In a preferred embodiment, the membrane displacement may for example be measured with a capacitor. Alternatively the membrane displacement can be measured by other means such as laser or a hall sensor.

In a preferred embodiment, the porous membrane in the implantable member comprises a hydrogel, which changes its porosity reversibly subject to analyte concentration. In case the analyte is glucose, the hydrogel advantageously contains a glucose responsive hydrogel. The glucose responsive hydrogel can be produced by using lectins (in particular concanavalin A), phenylboronic acid based hydrogels and other affinity receptors for glucose, or glucose oxidase or other molecules capable of binding glucose reversibly. In the case of other analytes, suitable affinity receptors known to the person skilled in the art and specific to the analyte such as binding proteins, antibodies (see for instance Miyata et al. 1999: A reversibly antigen-responsive hydrogel. Nature Vol. 399, pp. 766-769) or others can be used.

The hydrogel may be held in a tubular member comprising slots. The membrane advantageously is supported by the tubular structure of the implantable member, which may be made of any firm material, such as metallic, plastic, or ceramic materials. The implantable member may be implanted only partially into the patient's body, which is also referred to as minimally invasive in this field of technology.

The inventors have found a hydrogel described in relation to other applications and forms of use that is suitable for use in the present invention, in the particular case where the analyte is glucose. Tang et al. report the synthesis of a mechanically and chemically stable, glucose responsive hydrogel membrane, which can be cast in a number of mechanical forms. The response to changes in glucose concentration was demonstrated to be reversible in both directions, i.e. the transitions between gel and sol phase. Furthermore, the hydrogel showed negligible leakage of Concanavalin A over extended periods. The use of two dextran species with different molecular weights allowed greater control over the gel structure, such that property changes can be restricted to changes in internal porosity of the hydrogel (Tang et al. 2003: *A reversible hydrogel membrane and delivery of macromolecules*. Biotechnology and Bioengineering, Vol. 82, No. 1, Apr. 5, 2003).

Advantageously, concanavalin A is immobilized within the hydrogel, so that concanavalin A is prevented from entering the patient's body as it has been reported to have a toxic effect on humans. Methods to immobilize concanavalin A have been reported: Miyata et al. report the synthesis of a concanavalin A copolymerized glucosyloxyethyl methacrylate (GEMA) hydrogel, from which concanavalin A did not leak out and thus a reversible change in porosity of the porous membrane can be achieved (Miyata et al. 2004: *Glucose-responsive hydrogels prepared by copolymerization of a monomer with Con A*. Journal Biomaterial Science Polymer Edition, Vol. 15, No. 9, pp 1085-1098, 2004). Kim and Park reported the immobilization of concanavalin A to glucose-containing polymers (Kim J. J. and Park K. 2001: *Immobilization of Concanavalin A to glucose-containing polymers*. Macromolecular Symposium, No. 172, pp 95-102, 2001).

Within the scope of this invention however, the porous membrane may be made from various glucose responsive hydrogels that are per se known for glucose concentration measurement in glucose sensors for diabetes care and insulin delivery systems (See for instance: T. Miyata, T. Uragami, K. Nakamae Adv. Drug Deliver. Rev. 2002, 54, 79; Y. Qiu, K. Park Adv. Drug. Deliver. Rev. 2001, 53, 321; S. Chaterji, I. K. Kwon, K. park Prog. Polym. Sci. 2007, 32, 1083; N. A. Peppas J. Drug Del. Sci. Tech. 2004, 14, 247-256). Hydrogels are cross-linked polymeric matrices that absorb large amounts of water and swell. These materials may be physically and chemically cross-linked to maintain their structural integrity. Hydrogels can be sensitive to the conditions of the external environment in the presence of thermodynamically active functional groups. The swelling behavior of these gels may be dependent on pH, temperature, ionic strength, or solvent composition. These properties have been used to design stimuli responsive or "intelligent" hydrogels such as glucose-sensitive polymeric systems. (See for instance: G. Albin, T. A. Horbett, B. D. Ratner, J. Controlled Release, 1985, 2, 153; K. Ishihara, M. Kobayashi, I. Shinohara Polymer J. 1984, 16, 625).

Glucose Oxidase-Loaded Hydrogels:

The combination of a pH sensitive hydrogel with glucose oxidase (GOD) has been investigated to design glucose responsive hydrogels. Glucose is enzymatically converted by GOD to gluconic acid which lowers the pH of the environment. This enzyme has been combined to different types of pH sensitive hydrogels. For hydrogels that contain polycations, such as poly(N,N'-diethylaminoethyl methacrylate), the lowering of pH leads to hydrogel membrane swelling due to the ionization of the N,N'-diethylaminoethyl side chain. When a membrane swells, molecules diffuse more easily when compared to the collapsed state. If the hydrogel membranes contain polyanions, such as poly(methacrylic acid), pores are closed at high pH value due to electrostatic repulsion among the charges on the polymer chains. After lowering of the pH, pores are open because chains collapse due to the protonation of the methacrylic acid side chains. (Y. Ito, M. Casolaro, K. Kono, I. Yukio J. Controlled Release 1989, 10, 195)

Lectin-Loaded Hydrogels:

Another approach to design glucose responsive hydrogels consists in combining glucose containing polymers with carbohydrate-binding proteins (lectins) such as Concavalin A (Con A). The biospecific affinity binding between glucose receptors of Con A and glucose containing polymers leads to the formation of a gel capable of reversible sol-gel transition in response to free glucose concentration. A variety of natural glucose containing polymers has been used such as polysucrose, dextran, and glycogen (See for instance: M. J. Taylor, S. Tanna, J. Pharm. Pharmacol. 1994, 46, 1051; M. J. Taylor, S. Tanna, P. M. Taylor, G. Adams, J. Drug Target. 1995, 3, 209; S. Tanna, M. J. Taylor, J. Pharm. Pharmacol. 1997, 49, 76; S. Tanna, M. J. Taylor, Pharm Pharmacol. Commun. 1998, 4, 117; S. Tanna, M. J. Taylor, Proc. Int. Symp. Contr. Rel. Bioact. Mater. 1998, 25, 737B; S. Tanna, M. J. Taylor, G. Adams, J. Pharm. Pharmacol. 1999, 51, 1093). Additionally some synthetics polymers with well defined saccharide residues such as poly(2-glucosyloethyl methacrylate) (PGEMA) have been investigated. (K. Nakamae, T. Miyata, A. Jikihara, A. S. Hoffman J. Biomater. Sci. polym. Ed. 1994, 6, 79.)

Hydrogel with Phenylboronic Acid Moieties:

The fabrication and handling of glucose responsive hydrogels that incorporate proteins is difficult due to the instability of biological components. To overcome this problem, synthetic hydrogels that contain phenylboronic acid moieties have been investigated. Phenylboronic acid and its derivatives form complexes with polyol compounds, such as glucose in aqueous solution. Indeed, these Lewis acids can reversibly bind the cis-1,2- or -1,3-diols of saccharides covalently to form five- or six-membered rings. (C. J. Ward, P. Patel, T. D. James, Org. Lett. 2002, 4, 477.) The complex between phenylbornic acid and a polyol compound can be dissociated in the presence of a competing polyol compound which is able to form a stronger complex. Following this idea, the competitive binding of phenylboronic acid with glucose and poly (vinyl alcohol) was utilized to construct a glucose-sensitive system. (See for instance: A. Kikuchi, K. Suzuki, O. Okabayashi, H. Hoshino, K. Kataoka, Y. Sakurai, T. Okano Anal. Chem. 1996, 68, 823-828; K. Kataoka, H. Miyazaki Macromolecules 1994, 27, 1061-1062) In this case, the presence of free glucose resulted in swelling of the hydrogel. Despite promising results, the system described above cannot be used for in-vivo monitoring of glucose concentration for two reasons:

1) Physiological condition: The reverse binding of phenylbornic acid with polyol was not achieved at physiological conditions (temperature, ionic strength and pH values).

2) Selectivity: The binding of phenylboronic acid is not selective. Indeed, phenylboronic acids can form complexes with any saccharides possessing cis-1,2- or -1,3-diols (such as glucose, fructose and galactose and lactate). In healthy individuals glucose is normally present in the range 4-8 mM while fructose and galactose, the most abundant sugars after glucose, are usually present in physiological fluids at sub-mMol levels. (R. Badugu, J. R. Lakowicz, C. D. Geddes, Analyst 2004, 129, 516). Phenylboronic acids have a much greater affinity for fructose than glucose, (J. P. Lorand, J. O. Edwards, J. Am. Chem. Soc. 1959, 24, 769) a feature that may affect the accuracy of glucose measurement. Some formulations of hydrogels with phenylboronic acid moieties have been proposed in order to improve the selectivity of the gel and ensure a better reversibility at physiological conditions. One of the most promising formulations has been presented by Pritchard in 2006. (G. J. Worsley, G. A. Tourniaire, K. E. S. Medlock, F. K. Sartain, H. E. Harmer, M. Thatcher, A. M. Horgan, J. Pritchard Clinical Chem. 2007, 53, 1820-1826) A tertiary amine monomer (N-[3-(dimethylamino)propyl]-acrylamide) was copolymerized with 3-acrylamidophenyl-boronic acid to give a glucose responsive hydrogel with a specific affinity for glucose. In this case, an increase of the glucose concentration induces a contraction of the gel. The most probable explanation for the observed contraction is cross-linking of two neighboring boronic acid receptors with favorable stereochemistry by glucose to give a bis-boronate-glucose complex. A film of this glucose responsive hydrogel has been loaded with light sensitive crystals of AgBr to design a holographic glucose sensor which demonstrate its ability to measure glucose in human plasma. (See for instance: S. Tanna, T. S. Sahota, J. Clark, M. J. Taylor J. Drug Target. 2002, 10 411; S. Tanna, T. Sahota, J. Clark, M. J. Taylor, J. Pharm. Pharmacol. 2002, 54, 1461)

In a preferred method, the determined glucose concentration is calibrated with a further measurement, whereas the further measurement is performed after the glucose responsive porous membrane has been rinsed with the liquid, such that the further measurement determines the glucose concentration present in the liquid.

This is an important advantage of the present invention, which adds to its robustness and simplicity: in order to determine a reference value to which the measurements of the glucose concentration can be compared, a succession of discrete volumes of liquid are injected. After a number of units delivered, the porosity of the porous membrane has reached a value that is determined by the glucose concentration of the liquid contained in the medical device, which is a known value and thus can be used as a reference value. In order to calibrate the glucose measurement, simply the first measurement (which measures the glucose concentration of the solution surrounding the implantable member) of the above described series of measurements can be compared to the last measurement (which measures the known glucose concentration of the liquid present in the reservoir of the medical device). Thus, the glucose measurement may be adjusted against influences that may distort the measurement, such as changes in temperature, humidity, stability of electronics, material property such as aging of the hydrogel, and the like. This automatic calibration makes the medical device very simple and robust, as the measurement can be compared to a reference value by simply running a liquid delivery program as indicated above.

After not delivering any units, the porosity of the porous membrane will reach a value that is determined by the glucose concentration surrounding the membrane. The first unit delivered afterwards will be forced through the porous membrane with a porosity determined by the glucose concentration of the surrounding solution, and thus a new measuring cycle with integrated calibration as described above may be commenced.

If the medical device is used for drug administration, advantageously a separate channel for drug delivery is provided, as the flow capacity through the porous membrane is limited. This may be achieved by a second lumen in the implantable member, or by a second implantable member, or most preferably by a valve contained in the implantable member. The advantage of providing a valve is that only one pressure generating means, as well as only one implantable member, are required. For measuring the blood glucose level, the pressure generating means applies pressures below the opening pressure of the valve, so that the valve stays closed and the liquid can exit the implantable member only through the porous membrane. If drug administration is required, the pressure generating means raises the pressure above the opening pressure of the valve, so that a certain amount of drug contained in the liquid is administered. It is thus possible to administer a basal rate of insulin through the pores of the porous membrane and the bolus through the valve.

According to an embodiment of this invention, the liquid used in the medical device is a physiological aqueous solution, which is cheap, safe, and storable for a long period of time. Such a solution is employed if the medical device shall be used for continuous glucose monitoring but not for drug administration.

According to another embodiment of this invention, the liquid used in the medical device comprises a drug substance with regulatory functions on the blood glucose level of the patient, such as insulin or glucagon for example. In this case, the medical device is not only suitable for glucose monitoring, but also for the administration of medical compounds comprised in the liquid. One or more drug substances may be used, employing one or more reservoirs, and one or more pumps, thus allowing administering multiple drug substances independently.

For the administration of a drug, one or more implantable members may be provided, or multiple channels within one implantable member. In such a variant, one implantable member is used for drug administration and may be provided with a valve, whereas a second implantable member may contain a hydrogel as described above for blood glucose monitoring. Furthermore, the implantable member containing the hydrogel may be used for delivering a basal drug rate, whereas the implantable member containing the valve may be used for delivering a bolus drug rate.

According to this invention, the medical device may be used in a closed loop system, i.e. the monitoring of a physiological parameter is directly linked to the delivery of a drug that regulates said physiological parameter. However, a medical device according to this invention may also be used in a semi closed loop system, where the measurement of a physiological parameter is displayed by means of a display or other communication means, such that the patient receives information or advice concerning the drug delivery required in a given moment. Semi closed loop systems thus do not directly link monitoring and drug delivery, but allow the patient to interact and instruct or control the administration of the drug while receiving information from the monitoring unit.

The medical device may be able to communicate with a remote user device. This communication ability can be achieved either by cable or by wireless communication means. The remote user device may be an integral part of another device such as a wristwatch or a mobile phone, or it may constitute a separate device. Its function is to inform and warn the patient in connection with data determined by the medical device.

Additionally, there may further be an external alarm system, which may be in direct communication with the medical device or in communication with the remote user device. This external alarm system is suitable to inform doctors or hospitals about the condition of the patient, for example by using internet based services.

The medical device may advantageously comprise a disposable unit comprising the implantable member, glucose sensing device and liquid medicine reservoir, and a reusable unit comprising a graphical user interface, a signal processing circuit, and pump power supply and control means.

Further objects and advantageous aspects of the invention will be apparent from the claims and the following detailed description of an embodiment of the invention in conjunction of the drawings in which:

FIG. 2a illustrates a cross-sectional view of an implantable member without a valve according to an embodiment of the invention;

FIG. 2b illustrates a three-dimensional view of the implantable member without a valve of FIG. 2a;

FIG. 2c illustrates a three-dimensional partial cross-sectional view of the implantable member without a valve of FIG. 2a;

FIG. 3c illustrates a three-dimensional view of the implantable member with a valve of FIG. 3a;

FIG. 3d illustrates a three-dimensional partial cross-sectional view of the implantable member with a valve of FIG. 3a;

Figure 1A:
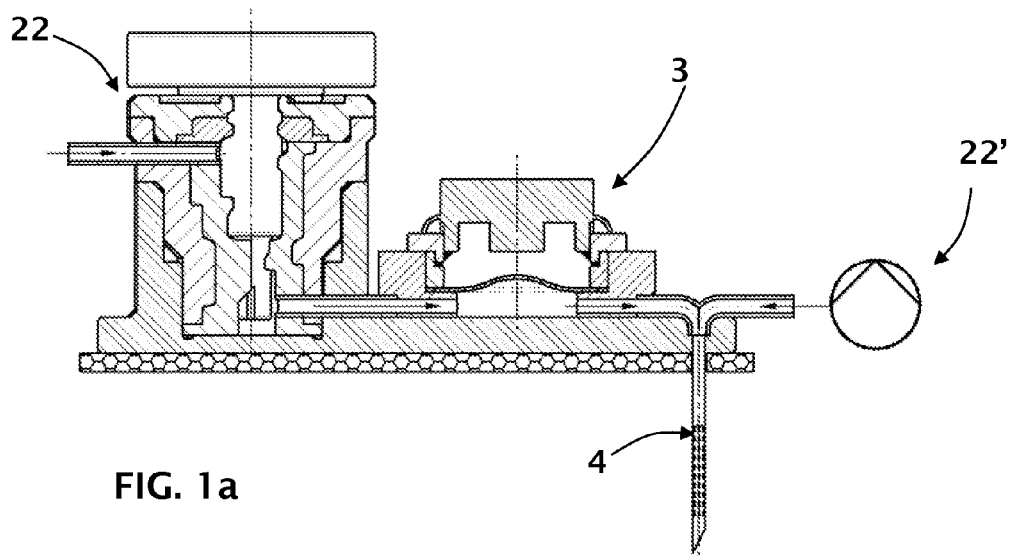
FIG. 1a illustrates a cross-sectional view of an embodiment of the invention comprising a pump, sensing means and an implantable member.
Figure 1B:
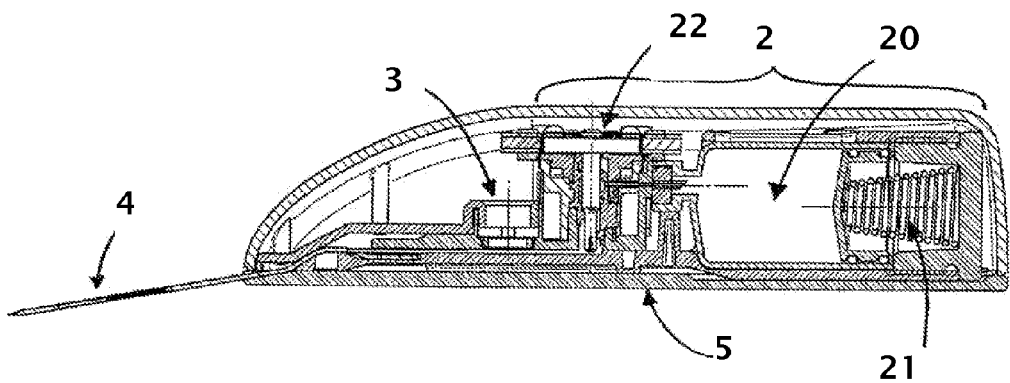
FIG. 1b illustrates a cross-sectional view of a medical device according to an embodiment of the invention comprising pressure generating means, sensing means and an implantable member.
Figure 1C:
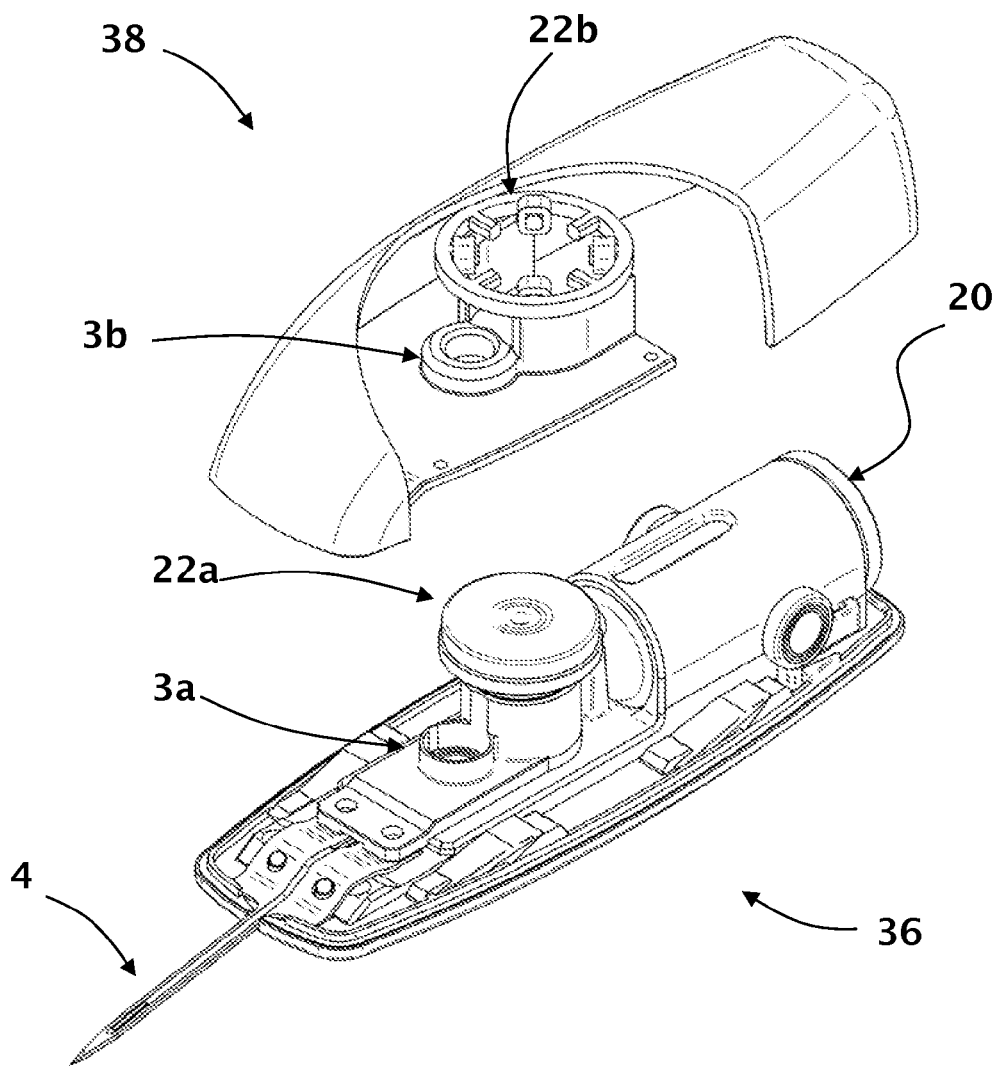
FIG. 1c illustrates a perspective exploded view of the medical device of FIG. 1b showing separable disposable and reusable units of the device.

Referring to the figures, in particular FIGS. 1a to 1c, an embodiment of a medical device 1 according to the present invention comprises a pressure generating means 2, a sensor 3 adapted to measure the flow resistance, and an implantable member 4.

The pressure generating means 2 delivers liquid towards the sensor 3, where the flow resistance subject to the porosity of the membrane in the implantable member 4 is measured.

Besides measuring the flow resistance, the sensor 3 conveys the liquid towards the implantable member 4.

The medical device 1 is preferably attached on to the skin of the patient, by using an adhesive base on the lower surface 5 of the medical device 1. The connection between the medical device 1 and the patient may be configured such that the connection lasts for several days, but may be removed from the skin at any time.

The design of the medical device 1 according to this invention is flexible. In a preferred embodiment, the medical device 1 is flat in order to ensure convenience in use, as it is intended to be worn below the clothing of the patient.

A preferred embodiment of pressure generating means 2 with a reservoir 20 possessing fixed walls is shown. The reservoir 20 may be a glass ampoule, which are frequently used as standards in insulin delivery devices. The reservoir 20 contains a plug that is forced towards the outlet of the reservoir. This is for instance achieved using a spring 21, which exerts pressure onto the plug.

Alternatively, the plug may be driven by a motor, which directly controls the liquid flow from the reservoir towards the sensor, such that between the reservoir and the sensor no additional pump is needed.

The liquid is further conveyed towards the sensor by a pump 22 (22a, 22b). The pump delivers the liquid in precise and interrupted units. Alternatively, a valve (not shown) may be used instead of the pump 22.

According to an alternative embodiment, the reservoir 20 is not put under pressure (not shown). In this case, the pump 22 sucks the liquid out of the reservoir, such that the plug is moved towards the outlet of the reservoir.

The reservoir 20 may alternatively be made of a flexible material (not shown). Flexible walls of the reservoir, which may be made of plastic material, allow pumping the liquid out of the reservoir without applying strong suction. A small piston pump as described in European patent application EP 1527793A1, may for instance be employed. Flexible reservoirs have the advantage that they may be provided in various shapes, such that the reservoir best fits into the medical device. This is of importance as the size of the medical device preferably is minimized for optimal wearing comfort.

Referring to FIG. 1c, the medical device may advantageously comprise a disposable unit 36 and a reusable unit 38. The disposable unit comprises the implantable member 4, a portion 3a of the flow resistance sensor 3, liquid medicine reservoir 20, and a portion 22a of the pump 22. The reusable unit 38 comprises (optionally) a user input and display interface (not shown), a signal processing circuit, a power supply, a complementary portion 3b of the flow resistance sensor 3, which includes sensor electronics, for example capacitor electrodes, and a complementary portion 22b of the pump 22, which includes pump drive means, for example electromagnets. The disposable and reusable units are separable, whereby the disposable unit can be removed after use from the reusable unit and replaced with a new disposable unit. Costly control and user interface components can thus be mounted in the reusable unit and preserved for multiple usage to reduce waste and save costs, without compromising on the safety of use of the components in the liquid medicine circuit (the implantable member and liquid medicine reservoir) that should be disposable.

In order to determine a reference value to which the measurements of the glucose concentration can be compared, a succession of discrete volumes of liquid are injected, for example 50 nano liters separated by 3 seconds, i.e. as soon as the flexible membrane has reached its relaxed state, a new discrete volume of liquid is delivered. Thus, a succession of fluid resistance measurements is performed rapidly, without long pauses in-between the measurements. After a number of pumping steps are delivered, for example 5 steps, the porosity of the porous membrane reaches a value that is determined by the glucose concentration of the liquid contained in the medical device, which is a known value and thus can be used as a reference value. The first step is used to measure the glucose concentration in the solution surrounding the implantable member, the second step will replace for example 80 percent of the equilibrated liquid in the needle lumen (in this example, the pump volume is equal to the active volume in the needle), and after the third step, only about 3 percent of the equilibrated liquid remains in the responsive region of the needle. Therefore, a small number of units pumped through the porous membrane, e.g. 5 steps, rinse the porous membrane and are enough to obtain a reference value for calibration.

In order to calibrate the glucose measurement, the first measurement (which measures the glucose concentration of the solution surrounding the implantable member) of the above described series of measurements can be compared to the last measurement (which measures the glucose concentration of the liquid present in the medical device).

After a pause, for example for 60 seconds, the porosity of the porous membrane has reached a value that is again determined by the glucose concentration surrounding the membrane. After about 60 seconds, given a pore size of 10 nm to 100 nm in the porous membrane, the liquid in the responsive part of the needle will reach almost the same glucose concentration as the concentration that is present in the surrounding solution. Therefore, a new measuring cycle with integrated calibration as described above may be commenced.

Typically, a new measuring cycle is not required more frequently than every five to ten minutes. The lag times as described above will thus not unduly restrict the application of the present invention for continuous glucose monitoring, especially in the view of the typical physiological lag time of 8-17 min. between interstitial and blood glucose as is commonly accepted in the literature.

Referring to FIGS. 2a to 2c, an embodiment of the implantable member 4 is shown. The implantable member has the shape of an injection needle, and is divided into two sections: A non-responsive part 6, and a responsive part 7. The wall of the non-responsive part is closed, and may be provided in a flexible material such as plastic in order to enhance the wearing comfort for the patient. The wall of the responsive part 7 contains holes 8, which are filled with a porous membrane 28. The fraction of the perforation surface area over the total surface area in the responsive part is preferably between 0.1 and 0.5 in order to obtain both enough surface area for the porous membrane as well as to obtain a needle that is robust enough to be introduced into a patient's skin. For instance, the fraction of the perforation surface area is between 0.2 and 0.3. The needle may be between 5 and 30 mm long, and have a diameter 30 of between 0.1 mm and 1.0 mm. The needle may be made of plastic material, but it may also consist of any other suitable material such as metallic materials, or ceramic materials.

The length of the needle part that is below the skin surface of the patient typically measures between 15 mm and 20 mm, whereas the responsive part measures 2 mm to 10 mm and the non-responsive part measures 7 mm to 13 mm. The thickness of the needle wall measures between 10 μm and 40 μm, and most preferably between 20 and 30 μm. The diameter of the needle typically measures 0.3 mm, defining the volume of the lumen 10 of the needle. The needle diameter and the length of the responsive part may be adapted to the pump volume (or vice versa) in order to ensure a convenient calibration method as described previously.

When filling the holes 8 with the porous membrane 28, a spacer may be inserted coaxially within the needle, the spacer having a slightly smaller diameter than the lumen diameter 31. After the porous membrane has been applied, the spacer is removed, and the lumen will then have a slightly smaller diameter 32.

As the concentration of glucose in the solution surrounding the implantable member 4 changes, the porosity of the porous membrane 28 contained in the holes 8 changes. Preferably the porous membrane contains immobilized concanavalin A and dextran molecules to form a hydrogel, which may be held by an additional supportive structure, such as nylon gauze support with a pore size of 0.1 mm (Tang et al. 2003: *A reversible hydrogel membrane and delivery of macromolecules*. Biotechnology and Bioengineering, Vol. 82, No. 1, Apr. 5, 2003). Other glucose responsive compounds, as described previously, may however also be used.

The hydrogel is capable of reversibly changing its structure depending on the glucose concentration present. Free glucose molecules competitively and specifically bind to immobilized concanavalin A molecules. A raise in glucose concentration will raise the number of concanavalin A binding sites occupied with glucose molecules and thus enlarging the size of the pores present in the hydrogel. If the glucose concentration decreases, glucose bound to concanavalin A will be replaced by dextran molecules which form an interlinked web-like structure, thus reducing the size of the pores present in the hydrogel. The response time for the porous membrane to reach equilibrium of glucose concentration according to the surrounding solution to 95 percent will typically measure 60 seconds.

Given a change in glucose concentration in the solution surrounding the implantable member 4 between 0 mmol/l and 30 mmol/l (the normal bandwidth of glucose concentration in the human blood is 4 mmol/l to 8 mmol/l), the effective pore size in the porous membrane would typically range from 10 nm to 100 nm in diameter.

Referring to FIGS. 3a to 3d, another embodiment of the implantable member 4 is shown. For the administration of medication, a valve 14 may be provided within the implantable member. The valve is disposed proximate a free end or tip of the implantable member. A support tube 9 is provided containing holes 8 in a responsive part 7 of the implantable member. A porous membrane containing a glucose responsive hydrogel 28 as previously described is mounted into the holes 8 of the support structure 9.

In order to allow the measurement of the flow resistance through the porous membrane, the valve 14 stays closed up to a critical pressure. When medication is to be administered, pressure generating means create a liquid pressure in the implantable device that exceeds the critical pressure so that the valve is opened and medication can be administered to the patient. Said critical pressure preferably is significantly higher than the pressure used for measuring flow resistance through the porous membrane. Typical values for measuring flow resistance range from 50 to 100 mbar, and thus typical critical pressure values in the valve range from 150 to 400 mbar. These numbers are simply for illustration purpose, other combinations of values that follow the same principle as described above are also contained within the spirit of this invention.

Figure 3A:
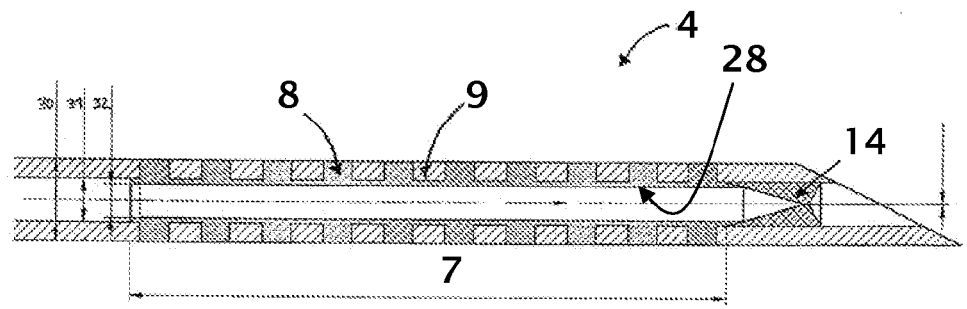
FIG. 3a illustrates a cross-sectional view of an implantable member with a valve according to an embodiment of the invention, where the valve is closed.
Figure 3B:
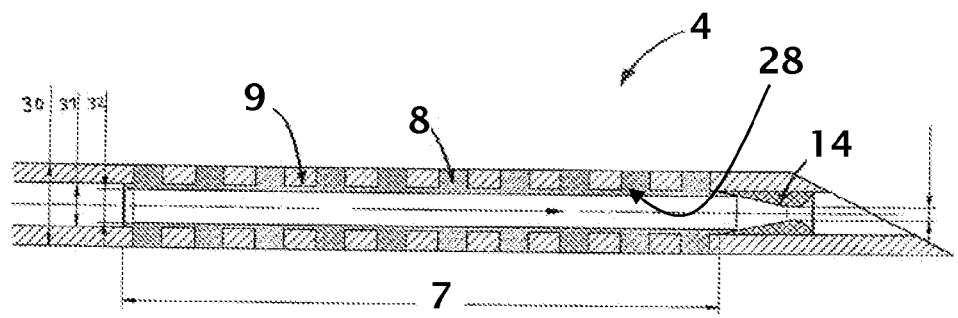
FIG. 3b illustrates a cross-sectional view of the implantable member with a valve of FIG. 3a, where the valve is open.

The valve 14 may comprise a pressure valve as shown in FIGS. 3a and 3b which may be made of elastic material (e.g. rubber). Preferably, the pressure valve comprises opposed elastic protuberances abutting each other under a pre-determined elastic pressure, whereby liquid at a pressure upstream of the valve greater than a pre-determined threshold, forces the protuberances apart to allow outflow of liquid. The valve may however also comprise other constructions, such as a flap valve, or spring and bullet valve, or any other kind of valve that fulfills the required function.

Figure 3E:
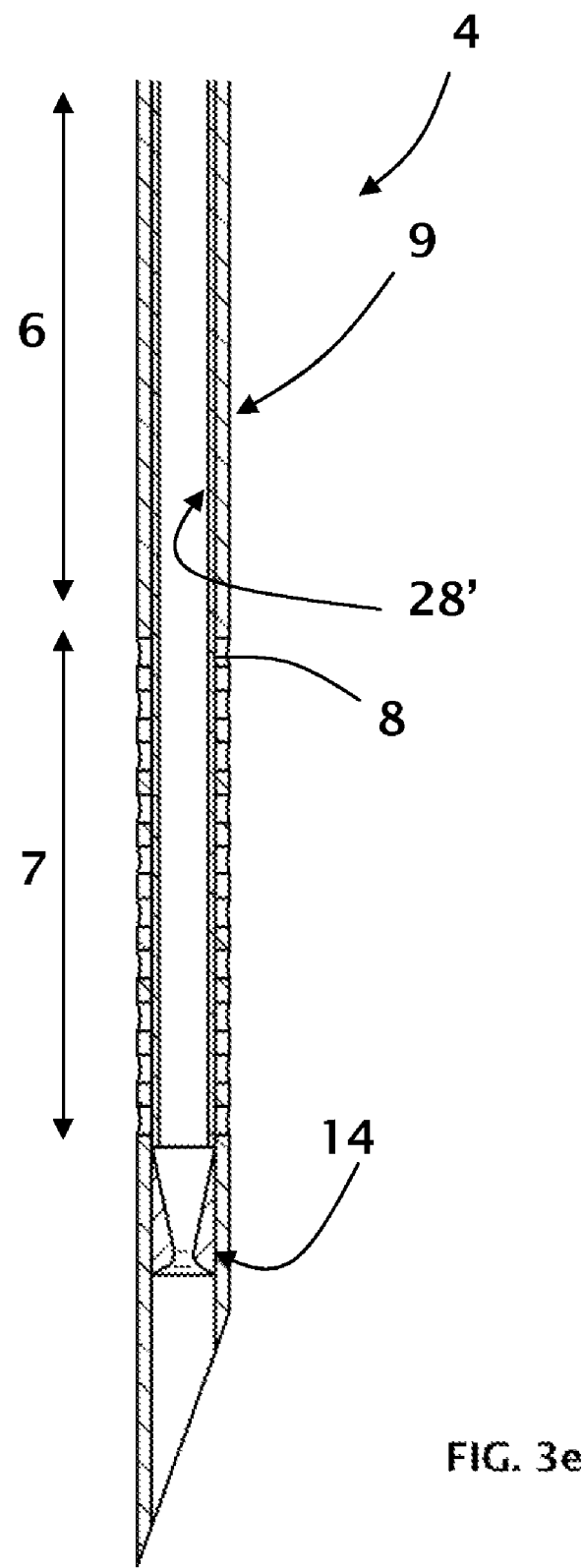
FIG. 3e illustrates a cross-sectional view of an implantable member with a valve according to another embodiment of the invention.

Referring to FIG. 3e, yet another embodiment of an implantable member 4 is shown, comprising a support structure, tube or sleeve 9 provided with holes 8 in a responsive part 7 of the implantable member and a glucose responsive porous membrane 28' in the form of a tube inserted in the support structure. The glucose responsive porous membrane tube 28' may thus be made separately from the support structure and assembled thereto. The tube 28' may comprise a glucose responsive hydrogel, as previously described, alone or incorporated in or on a non-glucose-responsive porous substrate. The substrate may advantageously comprise a cellulose fibre. The pore size of the cellulose fibre substrate is preferably in the range 10-50 nm, the wall thickness preferably 10-50 um, more preferably 20-30 um. The support sleeve 9 may be made for instance of a steel or titanium alloy with openings 8 of average diameter 20-1000 um, preferably 50-200 um. As described in relation to the other embodiments, for the administration of medication, a valve 14 may be provided within the implantable member. The valve 14 may be used for a bolus administration, whereas a basal rate may be administered through the porous membrane and/or through the valve.

Figure 4:
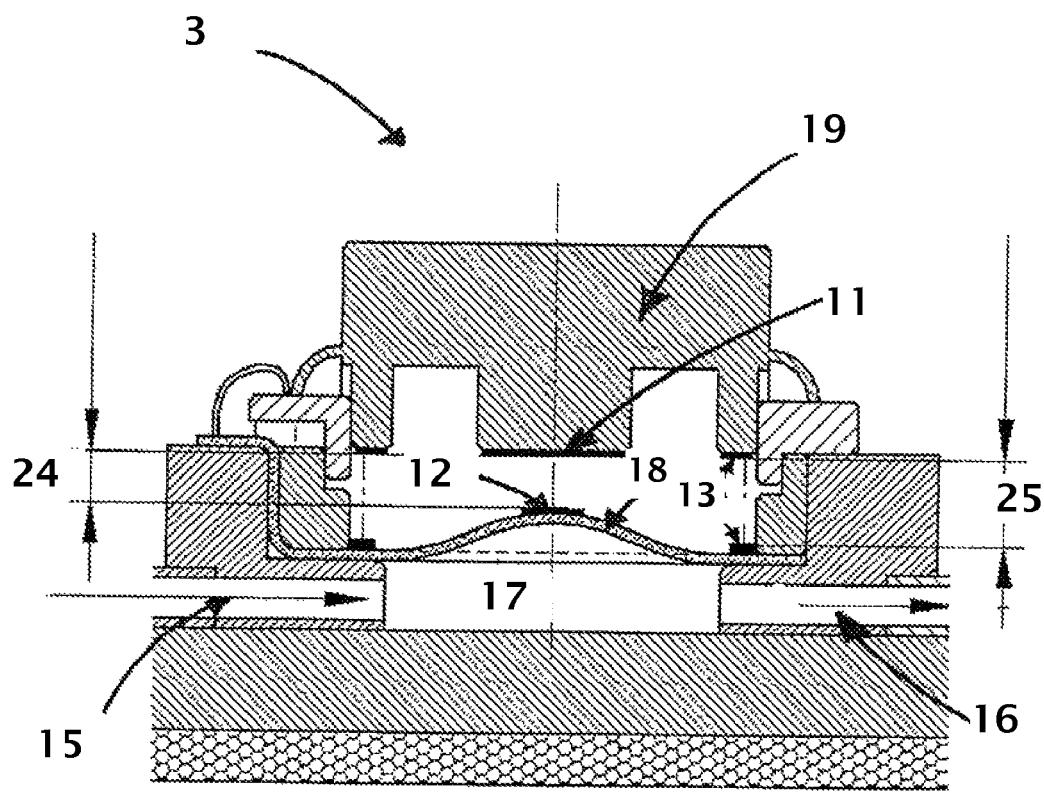
FIG. 4 illustrates a cross-sectional view of a sensor adapted to measure a flow resistance according to an embodiment of the invention.

Referring to FIG. 4, a preferred embodiment of the sensor 3 is shown. A precise amount of liquid delivered by the pressure generating means enters the sensor chamber 17 at the influx channel 15 and displaces a flexible membrane 18 comprised in the flow resistance sensor 3. Depending on the flow resistance subject to the porosity of the porous membrane in the implantable member, the decay (i.e. relaxation) behavior of the flexible membrane varies. The higher the flow resistance through the porous membrane, the longer it takes for the flexible membrane to reach its original position after displacement caused by the liquid delivered by the pressure generating means. While the flexible membrane 18 returns back to its rest position, liquid leaves the sensor chamber through the outlet channel 16 and thus the liquid is conveyed towards the implantable member.

To measure the displacement of the flexible membrane 18, advantageously a capacitor 19 is employed. A conductive coating, e.g. a gold coating, is provided on the upper surface of the flexible membrane forming a first capacitor electrode 12, another fixed position capacitor electrode 11 being placed at a certain distance over the flexible membrane. The capacitance value between the electrodes is representative of the amplitude (24, 25) of displacement of the flexible membrane. Advantageously, a reference capacitor electrode 13 is provided in order to adjust the measured value in case of an external interfering signal.

The medical device may be provided with more than one pump and liquid reservoir system to administer a second or further liquid medicine, for example glucagon in conjunction with insulin, such that the device may function as an artificial pancreas with blood glucose regulating and counter-regulating medicines. As illustrated in FIG. 1a, a second pump system 22' may be connected to the implantable member. The second pump system 22' may be constructed in the same manner as the pump 22, although without the flow resistance sensor 3 to minimize the dead volume in the path of the second pump system 22', and disposed adjacent the pump 22.

As mentioned above, the invention may be used of the sensing of analytes other than glucose by using a porous membrane responsive to the specific analyte to be measured.

The invention claimed is:

1. A medical device comprising:
    an implantable member comprising an analyte responsive porous membrane which reversibly changes its porosity subject to changes in analyte concentration occurring in the medium surrounding the implantable member;
    a pressure generating means configured to deliver a liquid to the analyte responsive porous membrane; and
    a sensor adapted to measure a flow resistance of said liquid through the analyte responsive porous membrane.

2. The medical device according to claim 1, wherein the pressure generating means delivers liquid in a succession of discrete amounts towards the glucose responsive porous membrane.

3. A medical device comprising:
    an implantable member comprising an analyte responsive porous membrane which reversibly changes its porosity subject to changes in analyte concentration occurring in the medium surrounding the implantable member;
    a pressure generating means configured to deliver a liquid to the analyte responsive porous membrane; and
    a sensor adapted to measure a flow resistance of said liquid through the analyte responsive porous membrane, wherein the sensor comprises a flexible membrane that is displaced upon liquid delivery, and a decay behavior of the flexible membrane is used to determine the flow resistance.

4. A medical device comprising:
    an implantable member comprising an analyte responsive porous membrane which reversibly changes its porosity subject to changes in analyte concentration occurring in the medium surrounding the implantable member;
    a pressure generating means configured to deliver a liquid to the analyte responsive porous membrane;
    a sensor adapted to measure a flow resistance of said liquid through the analyte responsive porous membrane; a disposable unit (36) and a reusable unit (38), the disposable unit comprising the implantable member (4), a portion (3a) of a flow resistance sensor (3), a liquid medicine reservoir (20) and a portion (22a) of a pump (22), and the reusable unit comprising a signal processing circuit, a power supply, a complementary portion (3b) of said flow resistance sensor, and a complementary portion (22b) of said pump.

5. A medical device comprising:
    an implantable member comprising an analyte responsive porous membrane which reversibly changes its porosity subject to changes in analyte concentration occurring in the medium surrounding the implantable member;
    a pressure generating means configured to deliver a liquid to the analyte responsive porous membrane; and
    a sensor adapted to measure a flow resistance of said liquid through the analyte responsive porous membrane, wherein the implantable member comprises a support tube (9) with holes (8) filled or lined with the analyte responsive porous membrane (28, 28').

6. The medical device according to claim 5, wherein the analyte responsive porous membrane (28') is in the form of a tube inserted in the support tube (9).

7. The medical device according to claim 6, wherein the analyte responsive porous membrane comprises a porous substrate incorporating an analyte responsive hydrogel.

8. The medical device according to claim 1, wherein the implantable member comprises a valve (14) positioned proximate a free end of the implantable member.

9. A medical device comprising:
    an implantable member comprising an analyte responsive porous membrane which reversibly changes its porosity subject to changes in analyte concentration occurring in the medium surrounding the implantable member;
    a pressure generating means configured to deliver a liquid to the analyte responsive porous membrane; and
    a sensor adapted to measure a flow resistance of said liquid through the analyte responsive porous membrane, wherein the implantable member comprises a valve (14) positioned proximate a free end of the implantable member, the valve comprising a pressure valve made of opposed abutting elastic protuberances.

10. The medical device according to claim 1, wherein the analyte is glucose and the liquid contains a drug capable of regulating blood glucose level in a patient.

11. The medical device according to claim 1, wherein the analyte is glucose and the porous membrane comprises a glucose responsive hydrogel selected from the group consisting of glucose-oxidase, lectin, and phenylboronic acid based hydrogels.

12. A method of operating a medical device comprising an analyte responsive porous membrane which changes its porosity subject to changes in an analyte concentration occurring in a solution surrounding the analyte responsive porous membrane, comprising:
    pumping a liquid in one or more discrete pre-determined volumes towards the analyte responsive porous membrane;
    measuring a flow resistance of the liquid through the analyte responsive porous membrane; and
    determining an analyte concentration based on the measured flow resistance.

13. The method according to claim 12, further including a calibration step comprising rinsing the analyte responsive porous membrane by pumping said liquid through the porous membrane and subsequently measuring a flow resistance of the liquid through the porous membrane.

14. The method according to claim 12, wherein the flow resistance is measured by a sensor comprising a flexible membrane that is displaced upon pumping the liquid, whereby a decay behavior of the flexible membrane is measured to determine a flow resistance.

15. The method according to claim 12, wherein the analyte is glucose and the analyte responsive porous membrane comprises a glucose responsive hydrogel selected from the group consisting of glucose-oxidase, lectin, and phenylboronic acid based hydrogels.

16. A method of measuring an analyte concentration, the method comprising:
    providing a medical device comprising an analyte responsive porous membrane which changes its porosity subject to changes in analyte concentration occurring in a solution surrounding the analyte responsive porous membrane;
    delivering a liquid in one or more discrete pre-determined volumes towards the analyte responsive porous membrane;
    measuring a flow resistance of the liquid through the analyte responsive porous membrane; and
    determining an analyte concentration based on the measured flow resistance.

17. The method according to claim 16, further including a calibration step comprising rinsing the analyte responsive porous membrane by pumping said liquid through the analyte responsive porous membrane and subsequently measuring a flow resistance of the liquid through the glucose responsive porous membrane.

18. The method according to claim 17, wherein the flow resistance is measured by a sensor comprising a flexible membrane that is displaced upon liquid delivery, whereby a decay behavior of the flexible membrane is used to determine a flow resistance.

19. The method according to claim 16, wherein the analyte is glucose and the glucose responsive porous membrane comprises a glucose responsive hydrogel selected from the group consisting of glucose-oxidase, lectin, and phenylboronic acid based hydrogels.

20. The method according to claim 16, wherein said analyte is glucose said method further comprising delivering a drug capable of influencing an glucose levels in a patient according to the measured glucose concentration in said patient that has been determined based on the measured flow resistance of said liquid.

21. The method according to claim 20, wherein the drug is delivered through a valve comprised in the implantable member.

22. The method according to claim 20, wherein a glucose responsive porous membrane is used to measure flow resistance of said liquid.

23. The method according to claim 22, wherein a basal rate of the drug is delivered through the glucose responsive porous membrane and a bolus rate of the drug is delivered through a valve.

24. The method according to claim 20, wherein the drug is delivered through a separate second implantable member or through a separated lumen within the implantable member.

25. The method according to claim 22, further including a patient interaction step comprising providing information on blood glucose level to the patient and receiving an instruction by the patient related to the delivery of the drug.

26. The method according to claim 22, wherein the delivered drug is any one or more of a substance capable of influencing blood glucose concentration, selected from the group consisting of insulin, glucagons, and amylin.

* * * * *